US011230522B2

(12) United States Patent
Greszta-Franz et al.

(10) Patent No.: US 11,230,522 B2
(45) Date of Patent: Jan. 25, 2022

(54) POLYASPARTIC ACID ESTER COMPOSITIONS WHICH CONTAIN POLYASPARTIC ACID ESTERS WITH PRIMARY AMINO GROUPS AND SMALL AMOUNTS OF FUMARIC ACID DIALKYL ESTERS

(71) Applicant: Covestro Deutschland AG, Leverkusen (DE)

(72) Inventors: Dorota Greszta-Franz, Solingen (DE); Jan Weikard, Leverkusen (DE); Matthias Wintermantel, Hürth (DE); Robert Maleika, Düsseldorf (DE); Thomas Klimmasch, Leverkusen (DE); Thomas Schuettler, Cologne (DE)

(73) Assignee: COVESTRO DEUTSCHLAND AG, Leverkusen (DE)

( * ) Notice: Subject to any disclaimer, the term of this patent is extended or adjusted under 35 U.S.C. 154(b) by 82 days.

(21) Appl. No.: 16/648,344

(22) PCT Filed: Sep. 14, 2018

(86) PCT No.: PCT/EP2018/074884
§ 371 (c)(1),
(2) Date: Mar. 18, 2020

(87) PCT Pub. No.: WO2019/057626
PCT Pub. Date: Mar. 28, 2019

(65) Prior Publication Data
US 2020/0216383 A1 Jul. 9, 2020

(30) Foreign Application Priority Data
Sep. 19, 2017 (EP) .................... 17191792

(51) Int. Cl.
*C07C 227/40* (2006.01)
*C07C 229/24* (2006.01)
*C07C 227/06* (2006.01)
*C07C 229/26* (2006.01)
*C08G 18/38* (2006.01)
*C08G 18/79* (2006.01)

(52) U.S. Cl.
CPC .......... *C07C 229/24* (2013.01); *C07C 227/06* (2013.01); *C07C 227/40* (2013.01); *C07C 229/26* (2013.01); *C08G 18/3821* (2013.01); *C08G 18/792* (2013.01)

(58) Field of Classification Search
CPC .... C07C 227/40; C07C 227/06; C07C 229/24
See application file for complete search history.

(56) References Cited

U.S. PATENT DOCUMENTS

| 5,126,170 | A | 6/1992 | Zwiener et al. |
| 5,214,086 | A | 5/1993 | Mormile et al. |
| 5,243,012 | A | 9/1993 | Wicks et al. |
| 5,364,955 | A | 11/1994 | Zwiener et al. |
| 5,412,056 | A | 5/1995 | Zwiener et al. |
| 5,559,204 | A | 9/1996 | Squiller et al. |
| 5,623,045 | A | 4/1997 | Zwiener et al. |
| 5,821,326 | A | 10/1998 | Kurek et al. |
| 6,458,293 | B1 * | 10/2002 | Roesler ................. C07C 229/24 252/182.23 |
| 6,559,274 | B2 | 5/2003 | Gertzmann et al. |
| 6,590,066 | B1 * | 7/2003 | Roesler .............. C08G 73/1092 528/328 |
| 6,737,500 | B1 * | 5/2004 | Roesler .............. C08G 18/3821 528/328 |
| 10,125,290 | B2 | 11/2018 | Enkisch-Krug et al. |
| 10,385,231 | B2 | 8/2019 | Enkisch-Krug et al. |
| 2004/0063894 | A1 | 4/2004 | Danielmeier et al. |
| 2016/0024339 | A1 | 1/2016 | Squiller et al. |

FOREIGN PATENT DOCUMENTS

| CN | 1952029 A | 4/2007 |
| CN | 101469246 A | 7/2009 |
| DE | 19701835 A1 | 7/1998 |
| DE | 102006002153 A | 7/2007 |
| EP | 0667362 A1 | 8/1995 |
| EP | 0893458 A1 | 1/1999 |
| WO | 0107399 A1 | 2/2001 |
| WO | WO 2014151307 A1 | 9/2014 |

OTHER PUBLICATIONS

International Search Report, PCT/EP2018/074884, dated Jan. 16, 2019, Authorized officer: Sandra Lanz.
Houben Weyl, Meth. d. Org. Chemie vol. 11/1, 272 (1957).
Usp. Khim. 1969, 38, 1933.

* cited by examiner

*Primary Examiner* — Michael L Leonard
(74) *Attorney, Agent, or Firm* — Jed C. Benson

(57) ABSTRACT

The present invention relates to polyaspartic acid ester compositions which contain polyaspartic acid esters with primary amino groups and small amounts of fumaric acid dialkyl esters, to a method for preparing same and the use thereof as a reactive component for polyisocyanates in two-component polyurethane systems.

6 Claims, No Drawings

POLYASPARTIC ACID ESTER COMPOSITIONS WHICH CONTAIN POLYASPARTIC ACID ESTERS WITH PRIMARY AMINO GROUPS AND SMALL AMOUNTS OF FUMARIC ACID DIALKYL ESTERS

CROSS-REFERENCE TO RELATED APPLICATION

This application is a national stage application under 35 U.S.C. § 371 of PCT/EP2018/074884, filed Sep. 14, 2018, which claims the benefit of European Application No. 17191792, filed Sep. 19, 2017, each of which is incorporated herein by reference.

FIELD

The present invention relates to polyaspartic ester compositions comprising polyaspartic esters having primary amino groups and small amounts of dialkyl fumarates, to a process for the production thereof, and to the use thereof as reactive components for polyisocyanates in two-component polyurethane systems.

BACKGROUND

Two-component (2K) coating compositions containing, as binder, a polyisocyanate component in combination with a component that is reactive toward isocyanates, in particular a polyhydroxyl component, have long been known. They are suitable for the production of high-quality coatings that can be tailored to make them hard, elastic, resistant to abrasion and solvents and, above all, weather-resistant.

Within this 2K polyurethane coating technology, certain ester-containing secondary polyamines that have become established in recent years, in combination with paint polyisocyanates, are particularly suitable as binders in low-solvent or solvent-free (high-solids) coating compositions and allow rapid hardening of the coatings at low temperatures.

These secondary polyamines are so-called polyaspartic esters, as described for example in EP0403921. Their use in 2K polyurethane coating compositions, either alone or in a mixture with further components that are reactive toward isocyanates, is described for example in EP0403921, EP0639628, EP0667362, EP0689881, U.S. Pat. No. 5,214,086, EP0699696, EP0596360, EP0893458, DE19701835, and U.S. Pat. No. 5,243,012.

The synthesis of the polyaspartic esters is known per se and is carried out through addition of primary polyamines onto an activated carbon-carbon double bond of vinylogous carbonyl compounds, as present for example in maleic or fumaric esters, which is adequately described in the literature (Hauben Weyl, Meth. d. Org. Chemie vol. 11/1, 272 (1957), Usp. Khim. 1969, 38, 1933). If only one amino group of the polyamine has reacted with the double bond of the vinylogous carbonyl compounds, this reaction can result in the formation, as a side product, of a polyaspartic ester having primary amino groups. In the commercially available polyaspartic esters, maleic ester is used as the vinylogous carbonyl compound. During production of a polyaspartic ester based on maleic ester, a retro-Michael addition can take place as a further undesired side reaction in which elimination of the polyamine results in the formation of dialkyl fumarate as a minor component. A typical production process for a polyaspartic ester therefore requires a storage time of 4-6 weeks once most of the starting materials have reacted with each other. During this time, the product undergoes so-called maturation, which is manifested by stabilization of the viscosity. Because conversion continues to increase during this time, the content of dialkyl fumarate falls too. This storage over several weeks results in significant logistics costs during production. Although the product is not shipped to the customer until the end of the storage period, it still contains substantial amounts of dialkyl fumarate, which can cause severe sensitization. Diethyl fumarate, for example, is classified as a VOC (volatile organic compound) and thus prevents provision of VOC-free coatings. Another disadvantage resulting from the presence of dialkyl fumarate is the lowering of the glass transition temperature of a coating film as a consequence of the plasticizing effect thereof.

As a consequence of the above-described disadvantages hitherto associated with polyaspartic ester compositions and the production thereof, there has long been a demand for polyaspartic ester compositions with a low dialkyl fumarate content that can be produced by a process that needs only a shortened maturation time or none at all.

There are in theory two options for modifying the process for producing polyaspartic ester compositions in order to give rise to polyaspartic ester compositions that are not subject to the above-mentioned disadvantages. The reaction time may be prolonged or the reaction temperature increased. The former is discounted on economic grounds. On the other hand, raising the reaction temperature for example to 100° C., or even to 80° C., leads to dramatic yellowing of the product.

EP0816326 discloses a process for accelerating the addition of the polyamine onto dialkyl maleate and for reducing the dialkyl fumarate content through the addition of a specific catalyst. Since the need for storage cannot be averted despite the use of a catalyst, this approach does not lead to an ultimately satisfactory result. EP 1197507 describes the addition of thiol compounds as scavengers for dialkyl fumarates. Because thiol compounds are known to cause a considerable odor nuisance, this is not a solution that can be implemented in practice either.

A theoretical option for distillative workup is mentioned for example in EP0403921. This describes a removal of dialkyl fumarate by distillation in a process in which an excess of dialkyl maleate is used. This disclosure does not specify examples or a method of distillation. Since an excess of diethyl maleate is used in this process, the worked-up product is not expected to contain significant amounts of polyaspartic esters having primary amino groups. This method has not gained acceptance, because the excessive amount of diethyl maleate used results in poor space-time yield and much waste, which is not economically justifiable.

DE102006002153 likewise describes a product that is produced using an excess of dialkyl maleate and subsequent removal of dialkyl fumarate by distillation. This is a diaspartic ester that is free of primary amino groups.

The production of amino-functional aspartic esters is known in principle. WO15130501 and WO15130502 disclose polyaspartic ester compositions that contain between 15 and 30% of aspartic esters having primary amino groups (measured as area-% in the gas chromatogram). However, neither document identifies any advantage arising from an increased content of aspartic esters having primary amino groups, and polyaspartic ester compositions with an acceptable pot life were achieved only by further reaction with preferably cycloaliphatic polyisocyanates. Given the conventional production process, the coating compositions thus produced can be assumed not to have a reduced content of diethyl fumarate.

SUMMARY

In the context of the present invention, polyaspartic ester compositions can be produced that have a content of 1% to 20% of polyaspartic esters having primary amino groups (measured as area-% in the gas chromatogram) and a reduced dialkyl fumarate content of from 0.01% by weight to 3% by weight, while at the same time overcoming the disadvantages of polyaspartic ester compositions known from the prior art. These compositions according to the invention could be produced via a process with and without a storage process.

It has been found that thin-film distillation of a non-matured polyaspartic ester composition (i.e. immediately after production) results in a product containing levels of dialkyl fumarate below 1%. Since the reaction conversion at the time of the thin-film distillation is about 90%, the proportion of polyaspartic esters having primary amino groups is markedly higher in the product than in the conventional polyaspartic ester composition. The high proportion of polyaspartic esters having primary amino groups could be expected to result in a shorter pot life. However, it was surprisingly found that the pot life of polyaspartic ester compositions according to the present invention does not differ from the pot life of a conventionally produced polyaspartic ester composition. Moreover, the polyaspartic ester compositions according to the present invention show accelerated drying and improved resistance to water of condensation as further technical advantages. The thin-film distillation process can also be applied to matured polyaspartic ester compositions. The advantage in this case is not the omission of maturation, but the reduced amount of dialkyl fumarate and faster drying on account of the increased proportion of polyaspartic esters having a primary amino group The present invention provides a composition comprising one or more polyaspartic esters of the general formula (I)

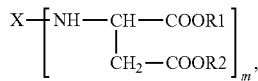

in which

X is an m-valent organic radical, optionally containing one or more heteroatoms, as can be obtained by removing the primary amino groups from a corresponding polyamine that has (cyclo)aliphatically or araliphatically attached amino groups and is in the molecular weight range from 60 to 6000 g/mol, and which may contain further functional groups that are reactive toward isocyanate groups and/or inert at temperatures of up to 100° C., R1 and R2 are identical or different organic radicals each having 1 to 18 carbon atoms, m is an integer >1, and one or more polyaspartic esters having a primary amino group that are of the general formula (II)

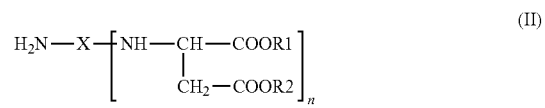

in which n is m−1,

X and radicals R1 and R2 have the meanings defined above, characterized in that the proportion of the compound of the general formula (II) corresponds to from 1% to 20% of the GC surface area (measured as area-% in the gas chromatogram), wherein the sum of the GC surface areas of the two compounds of the general formula (I) and (II) is 100% and dialkyl fumarate is present in a proportion of 0.01 to 3% by weight.

DETAILED DESCRIPTION

Preference is given to the polyaspartic ester compositions according to the invention in which R1 and R2 are identical or different alkyl radicals each having 1 to 18 carbon atoms, preferably identical or different alkyl radicals each having 1 to 8 carbon atoms and most preferably in each case alkyl radicals such as methyl, ethyl, propyl, isopropyl, butyl or isobutyl radicals. Very particular preference is given to ethyl.

Polyaspartic ester compositions according to the invention are those in which X is organic radicals obtained by removing the primary amino groups from a corresponding (cyclo)aliphatically or araliphatically attached polyamine having primary amino groups, selected from the following group: all known polyamines having primary amino groups that conform to the general formula (III). Examples include the following compounds: ethylenediamine, 1,2-diaminopropane, 1,4-diaminobutane, 1,5-diaminopentane, 2,5-diamino-2,5-dimethylhexane, 1,5-diamino-2-methylpentane (Dytek®A, DuPont), 1,6-diaminohexane, 2,2,4- and/or 2,4,4-trimethyl-1,6-diaminohexane, 1,11-diaminoundecane, 1,12-diaminododecane or triaminononane, etheramines such as 4,9-dioxadodecane-1,12-diamine, 4,7,10-trioxatridecane-1,13-diamine or higher-molecular-weight polyether polyamines having aliphatically attached primary amino groups, for example those marketed under the Jeffamine® name by Huntsman. Also employable are aliphatic polycyclic polyamines such as tricyclodecanebismethylamine (TCD diamine) or bis(aminomethyl)norbornanes, amino-functional siloxanes, for example diaminopropylsiloxane G10 DAS (from Momentive), oleoalkyl-based amines, for example Fentamine from Solvay, dimeric fatty acid diamines such as Priamine from Croda.

Preference is given to the polyaspartic ester compositions according to the invention in which X is organic radicals obtained by removing the primary amino groups from one of the polyamines of the general formula (III) in which m=2 and X is a cyclic hydrocarbon radical containing at least one cyclic carbon ring. Examples of diamines usable with particular preference are 1-amino-3,3,5-trimethyl-5-aminomethylcyclohexane (IPDA), 2,4- and/or 2,6-hexahydrotolylenediamine (H6-TDA), isopropyl-2,4-diaminocyclohexane and/or isopropyl-2,6-diaminocyclohexane, 1,3-bis(aminomethyl)cyclohexane, 2,4'-, and/or 4,4'-diaminodicyclohexylmethane, 3,3'-dimethyl-4,4'-diaminodicyclohexylmethane (Laromin® C 260, BASF AG), the isomeric diaminodicyclohexylmethanes substituted in the ring with a methyl group (=C-monomethyl-diaminodicyclohexylmethanes), 3(4)-aminomethyl-1-methylcyclohexylamine (AMCA), and also araliphatic diamines such as 1,3-bis(aminomethyl)benzene or m-xylylenediamine.

Likewise preferred are the polyaspartic ester compositions according to the invention in which X is organic radicals obtained by removing the primary amino groups from one of the polyamines of the general formula (III) selected from the following group: polyether polyamines having aliphatically attached primary amino groups, 1,2-diaminopropane, 1,4-diaminobutane, 1,6-diaminohexane, 1,5-diamino-2-methylpentane, 2,5-diamino-2,5-dimethylhexane, 2,2,4- and/or 2,4,4-trimethyl-1,6-diaminohexane, 1,11-diaminoundecane, 1,12-diaminododecane, 1-amino-3,3,5-trimethyl-5-aminomethylcyclohexane, 2,4- and/or 2,6-hexahydrotolylenediamine, 1,5-diaminopentane, 2,4'- and/or 4,4'-diaminodicyclohexylmethane or 3,3'-dimethyl-4,4'-diaminodicyclohexylmethane.

Particular preference is given to 3,3'-dimethyl-4,4'-diaminodicyclohexylmethane, 1,5-diaminopentane, 2,4'- and/or 4,4'-diaminodicyclohexylmethane, 1,5-diamino-2-methylpentane, and very particular preference to the use of 2,4'- and/or 4,4'-diaminodicyclohexylmethane.

Particular preference is given to the polyaspartic ester compositions according to the invention in which X is organic radicals obtained by removing the primary amino groups from one of the polyamines of the general formula (III) selected from the following group: polyether polyamines having aliphatically attached primary amino groups, 1,2-diaminopropane, 1,4-diaminobutane, 1,5-diaminopentane, 1,6-diaminohexane, 1,5-diamino-2-methylpentane, 2,5-diamino-2,5-dimethylhexane, 2,2,4- and/or 2,4,4-trimethyl-1,6-diaminohexane, 1,11-diaminoundecane, 1,12-diaminododecane, 1-amino-3,3,5-trimethyl-5-aminomethylcyclohexane, 2,4- and/or 2,6-hexahydrotolylenediamine, 2,4'- and/or 4,4'-diaminodicyclohexylmethane or 3,3'-dimethyl-4,4'-diaminodicyclohexylmethane.

Most preferred are the polyaspartic ester compositions according to the invention in which X is organic radicals obtained by removing the primary amino groups from one of the polyamines of the general formula (III) selected from the following group: 3,3'-dimethyl-4,4'-diaminodicyclohexylmethane, 2,4'- and/or 4,4'-diaminodicyclohexylmethane, 1,5-diamino-2-methylpentane.

Preferably, m is an integer >1 and is more preferably 2.

Preference is given to the polyaspartic ester compositions according to the invention containing a proportion of 1% to 20%, preferably 4% to 20%, more preferably up to 4% to 15%, of the GC surface area (measured as area-% in the gas chromatogram) of the compound of the general (II) corresponds, wherein the sum of the GC surface areas of the two compounds of the general formula (I) and (II) is 100%.

Preference is given to the polyaspartic ester compositions according to the invention containing a proportion of 0.01 to 3% by weight, preferably 0.01 to 1% by weight, more preferably 0.01 to 0.1% by weight, of dialkyl fumarate.

Preference is likewise given to the polyaspartic ester compositions according to the invention containing a proportion of 0.01 to 0.99% by weight of dialkyl fumarate.

The present invention particularly preferably provides a composition comprising one or more polyaspartic esters of the general formula (I),
in which
X is an m-valent organic radical optionally containing one or more heteroatoms, as obtained by removing primary amino groups from polyether polyamines having aliphatically attached primary amino groups, 1,2-diaminopropane, 1,4-diaminobutane, 1,5-diaminopentane, 1,6-diaminohexane, 1,5-diamino-2-methylpentane, 2,5-diamino-2,5-dimethylhexane, 2,2,4- and/or 2,4,4-trimethyl-1,6-diaminohexane, 1,11-diaminoundecane, 1,12-diaminododecane, 1-amino-3,3,5-trimethyl-5-aminomethylcyclohexane, 2,4- and/or 2,6-hexahydrotolylenediamine, 2,4'- and/or 4,4'-diaminodicyclohexylmethane or 3,3'-dimethyl-4,4'-diaminodicyclohexylmethane, R1 and R2 are identical or different alkyl radicals each having 1 to 8 carbon atoms, m is an integer >1,
and
one or more polyaspartic esters having a primary amino group that are of the general formula (II), in which
n is m−1,
X and radicals R1 and R2 have the meanings defined above,
characterized in that the proportion of the compound of the general formula (II) corresponds to from 4% to 20% of the GC surface area (measured as area-% in the gas chromatogram), wherein the sum of the GC surface areas of the two compounds of the general formula (I) and (II) is 100% and dialkyl fumarate is present in a proportion of 0.01 to 1% by weight.

The present invention most preferably provides a composition comprising one or more polyaspartic esters of the general formula (I), in which
X is an m-valent organic radical as can be obtained by removing primary amino groups from 3,3'-dimethyl-4,4'-diaminodicyclohexylmethane, 2,4'- and/or 4,4'-diaminodicyclohexylmethane, 1,5-diamino-2-methylpentane,
R1 and R2 are identical or different alkyl radicals selected from the group consisting of methyl, ethyl, propyl, isopropyl, butyl or isobutyl radicals,
m is 2,
and
one or more polyaspartic esters having primary amino groups of the general formula (II), in which
n is m−1,
X and radicals R1 and R2 have the meanings defined above,
characterized in that the proportion of the compound of the general formula (II) corresponds to from 4% to 15% of the GC surface area (measured as area-% in the gas chromatogram), wherein the sum of the GC surface areas of the two compounds of the general formula (I) and (II) is 100% and dialkyl fumarate is present in a proportion of 0.01 to 0.1% by weight.

The present invention particularly preferably further provides a composition comprising one or more polyaspartic esters of the general formula
(I),
in which
X is an m-valent organic radical as can be obtained by removing primary amino groups from 3,3'-dimethyl-4,4'-diaminodicyclohexylmethane, 2,4'- and/or 4,4'-diaminodicyclohexylmethane,
R1 and R2 are ethyl radicals,
m is 2,
and
one or more polyaspartic esters having a primary amino group that are of the general formula (II), in which n is m−1, X and radicals R1 and R2 have the meanings defined above, characterized in that the proportion of the compound of the general formula (II) corresponds to from 4% to 15% of the GC surface area (measured as area-% in the gas chromatogram), the proportion of the two compounds of the general formula (I) and (II), wherein the sum of the GC surface areas of the two compounds of the general formula (I) and (II) is 100% and dialkyl fumarate is present in a proportion of 0.01 to 0.1% by weight.

The present invention particularly preferably further provides a composition comprising one or more polyaspartic esters of the general formula (I)

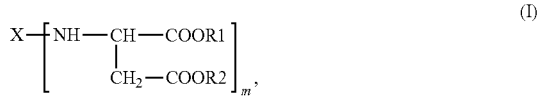

in which
X is an m-valent organic radical, optionally containing one or more heteroatoms, as can be obtained by removing the primary amino groups from a corresponding polyamine that has (cyclo)aliphatically or aralipathically attached amino groups and is in the molecular weight range from 60 to 6000 g/mol, and which may contain further functional groups that are reactive toward isocyanate groups and/or inert at temperatures of up to 100° C., R1 and R2 are identical or different organic radicals each having 1 to 18 carbon atoms, m is an integer >1, and one or more polyaspartic esters having primary amino groups of the general formula (II)

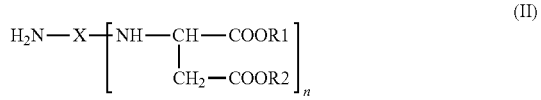

in which
n is m−1,

X and radicals R1 and R2 have the meanings defined above, characterized in that the proportion of the compound of the general formula (II) corresponds to from 4% to 15% of the GC surface area (measured as area-% in the gas chromatogram), wherein the sum of the GC surface areas of the two compounds of the general formula (I) and (II) is 100% and dialkyl fumarate is present in a proportion of 0.01 to 1% by weight.

The present invention particularly preferably further provides a composition comprising one or more polyaspartic esters of the general formula (I)

in which
X is an m-valent organic radical, optionally containing one or more heteroatoms, as can be obtained by removing the primary amino groups from a corresponding polyamine that has (cyclo)aliphatically or aralipathically attached amino groups and is in the molecular weight range from 60 to 6000 g/mol, and which may contain further functional groups that are reactive toward isocyanate groups and/or inert at temperatures of up to 100° C., R1 and R2 are identical or different organic radicals each having 1 to 18 carbon atoms, m is an integer >1, and one or more polyaspartic esters having primary amino groups of the general formula (II)

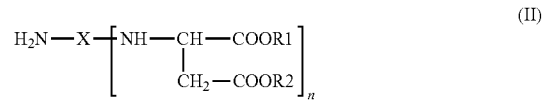

in which
n is m−1,

X and radicals R1 and R2 have the meanings defined above, characterized in that the proportion of the compound of the general formula (II) corresponds to from 4% to 15% of the GC surface area (measured as area-% in the gas chromatogram), the proportion of the two compounds of the general formula (I) and (II), wherein the sum of the GC surface areas of the two compounds of the general formula (I) and (II) is 100% and dialkyl fumarate is present in a proportion of 0.01 to 0.99% by weight.

Preference is given to polyaspartic ester compositions according to the invention that have a platinum-cobalt color index of ≤100, more preferably ≤50. The platinum-cobalt color index is measured in accordance with DIN EN ISO 6271:2016-05.

The invention further provides a process for producing the composition comprising one or more polyaspartic esters of the general formula (I)

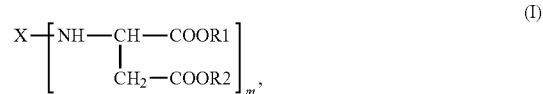

in which
X is an m-valent organic radical, optionally containing one or more heteroatoms, as can be obtained by removing the primary amino groups from a corresponding polyamine that has (cyclo)aliphatically or aralipathically attached amino groups and is in the molecular weight range from 60 to 6000 g/mol, and which may contain further functional groups that are reactive toward isocyanate groups and/or inert at temperatures of up to 100° C., R1 and R2 are identical or different organic radicals, preferably identical or different alkyl radicals each having 1 to 18 carbon atoms, and most preferably identical or different alkyl radicals each having 1 to 8 carbon atoms, m is an integer >1,
and
one or more polyaspartic esters having a primary amino group that are of the general formula (II)

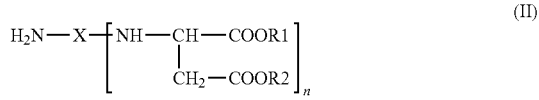

in which
  n is m−1,
  X and radicals R1 and R2 have the meanings defined above,
produced by reacting polyamines of the general formula (III),

in which X and m have the meaning defined above,
with compounds of the general formula (IV)

in which the radicals R1 and R2 have the meaning defined above,
and removal by distillation of the unreacted proportion of the compound of the general formula (IV),
characterized in that the resulting polyaspartic ester composition contains a proportion of the compound of the general formula (II) of from 1% to 20% of the GC surface area (measured as area-% in the gas chromatogram), which corresponds to the proportion of the two compounds of the general formula (I) and (II), wherein the sum of the GC surface areas of the two compounds of the general formula (I) and (II) is 100%, and dialkyl fumarate in a proportion of 0.01 to 3% by weight.

The present invention preferably further provides the process disclosed above for producing the composition comprising one or more polyaspartic esters of the general formula (I), in which
  X is an m-valent organic radical, optionally containing one or more heteroatoms, as obtained by removing primary amino groups from polyether polyamines having aliphatically attached primary amino groups, 1,2-diaminopropane, 1,4-diaminobutane, 1,5-diaminopentane, 1,6-diaminohexane, 1,5-diamino-2-methylpentane, 2,5-diamino-2,5-dimethylhexane, 2,2,4- and/or 2,4,4-trimethyl-1,6-diaminohexane, 1,11-diaminoundecane, 1,12-diaminododecane, 1-amino-3,3,5-trimethyl-5-aminomethylcyclohexane, 2,4- and/or 2,6-hexahydrotolylenediamine, 2,4'- and/or 4,4'-diamino-dicyclohexylmethane or 3,3'-dimethyl-4,4'-diaminodicyclohexylmethane,
  R1 and R2 are identical or different alkyl radicals each having 1 to 8 carbon atoms,
  m is an integer >1,
and
one or more polyaspartic esters having a primary amino group that are of the general formula (II), in which
  n is m−1,
  X and radicals R1 and R2 have the meanings defined above,
produced by reacting polyamines of the general formula (III), in which X and m have the meaning defined above, with compounds of the general formula (IV), in which the radicals R1 and R2 have the meaning defined above
and removal by distillation of the unreacted proportion of the compound of the general formula (IV),
characterized in that the resulting polyaspartic ester composition contains a proportion of the compound of the general formula (II) of from 4% to 20% of the GC surface area (measured as area-% in the gas chromatogram), which corresponds to the proportion of the two compounds of the general formula (I) and (II), wherein the sum of the GC surface areas of the two compounds of the general formula (I) and (II) is 100%, and dialkyl fumarate in a proportion of 0.01 to 1% by weight.

The present invention preferably further provides the process disclosed above for producing the composition comprising one or more polyaspartic esters of the general formula (I), in which
  X is an m-valent organic radical as can be obtained by removing primary amino groups from 3,3'-dimethyl-4,4'-diaminodicyclohexylmethane, 2,4'- and/or 4,4'-diaminodicyclohexylmethane, 1,5-diamino-2-methylpentane,
  R1 and R2 are identical or different alkyl radicals selected from the group consisting of methyl, ethyl, propyl, isopropyl, butyl or isobutyl radicals,
  m is 2,
and
one or more polyaspartic esters having a primary amino group that are of the general formula (II), in which
  n is m−1,
  X and radicals R1 and R2 have the meanings defined above,
produced by reacting polyamines of the general formula (III), in which X and m have the meaning defined above, with compounds of the general formula (IV), in which the radicals R1 and R2 have the meaning defined above
and removal by distillation of the unreacted proportion of the compound of the general formula (IV),
characterized in that the resulting polyaspartic ester composition contains a proportion of the compound of the general formula (II) of from 4% to 15% of the GC surface area (measured as area-% in the gas chromatogram), which corresponds to the proportion of the two compounds of the general formula (I) and (II), wherein the sum of the GC surface areas of the two compounds of the general formula (I) and (II) is 100%, and dialkyl fumarate in a proportion of 0.01 to 0.1% by weight.

The invention preferably further provides a process for producing the composition comprising one or more polyaspartic esters of the general formula (I)

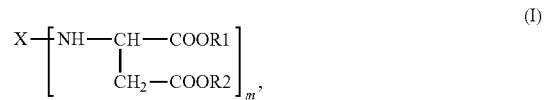

in which
  X is an m-valent organic radical, optionally containing one or more heteroatoms, as can be obtained by removing the primary amino groups from a corresponding polyamine that has (cyclo)aliphatically or araliphatically attached amino groups and is in the molecular weight range from 60 to 6000 g/mol, and which may contain further functional groups that are reactive toward isocyanate groups and/or inert at temperatures of up to 100° C., R1 and R2 are identical or different organic radicals, preferably identical or different alkyl radicals each having 1 to 18 carbon atoms, and most preferably identical or different alkyl radicals each having 1 to 8 carbon atoms, m is an integer >1, and one or more polyaspartic esters having a primary amino group that are of the general formula (II)

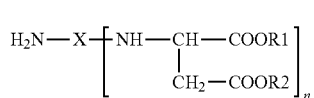
(II)

in which n is m−1,

X and radicals R1 and R2 have the meanings defined above, produced by reacting polyamines of the general formula (III),

(III)

in which X and m have the meaning defined above, with compounds of the general formula (IV)

R1OOC—CH=CH—COOR2    (IV), in which the radicals R1 and R2 have the meaning defined above, and removal by distillation of the unreacted proportion of the compound of the general formula (IV), characterized in that the resulting polyaspartic ester composition contains a proportion of the compound of the general formula (II) of from 4% to 15% of the GC surface area (measured as area-% in the gas chromatogram), which corresponds to the proportion of the two compounds of the general formula (I) and (II), wherein the sum of the GC surface areas of the two compounds of the general formula (I) and (II) is 100%, and dialkyl fumarate in a proportion of 0.01 to 1% by weight.

The invention preferably further provides a process for producing the composition comprising one or more polyaspartic esters of the general formula (I)

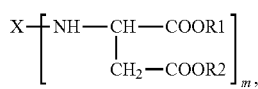
(I)

in which

X is an m-valent organic radical, optionally containing one or more heteroatoms, as can be obtained by removing the primary amino groups from a corresponding polyamine that has (cyclo)aliphatically or araliphatically attached amino groups and is in the molecular weight range from 60 to 6000 g/mol, and which may contain further functional groups that are reactive toward isocyanate groups and/or inert at temperatures of up to 100° C., R1 and R2 are identical or different organic radicals, preferably identical or different alkyl radicals each having 1 to 18 carbon atoms, and most preferably identical or different alkyl radicals each having 1 to 8 carbon atoms, m is an integer >1, and one or more polyaspartic esters having a primary amino group that are of the general formula (II)

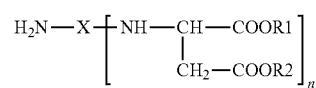
(II)

in which n is m−1,

X and radicals R1 and R2 have the meanings defined above, produced by reacting polyamines of the general formula (III),

(III)

in which X and m have the meaning defined above, with compounds of the general formula (IV)

R1OOC—CH=CH—COOR2    (IV), in which the radicals R1 and R2 have the meaning defined above, and removal by distillation of the unreacted proportion of the compound of the general formula (IV), characterized in that the resulting polyaspartic ester composition contains a proportion of the compound of the general formula (II) of 4% to 15% of the GC surface area (measured as area-% in the gas chromatogram), wherein the sum of the GC surface areas of the two compounds of the general formula (I) and (II) is 100%, and contains dialkyl fumarate in a proportion of 0.01 to 0.99% by weight.

The present invention preferably further provides the process disclosed above for producing the composition comprising one or more polyaspartic esters of the general formula (I), in which X is an m-valent organic radical, as can be obtained by removing primary amino groups from 2,4'- and/or 4,4'-diaminodicyclohexylmethane, R1 and R2 are ethyl radicals, m is 2, and one or more polyaspartic esters having a primary amino group that are of the general formula (II), in which n is m−1, X and radicals R1 and R2 have the meanings defined above, produced by reacting polyamines of the general formula (III), in which X and m have the meaning defined above, with compounds of the general formula (IV), in which the radicals R1 and R2 have the meaning defined above and removal by distillation of the unreacted proportion of the compound of the general formula (IV), characterized in that the resulting polyaspartic ester composition contains a proportion of the compound of the general formula (II) of 4% to 15% of the GC surface area (measured as area-% in the gas chromatogram), corresponds, wherein the sum of the GC surface areas of the two compounds of the general formula (I) and (II) is 100%, and dialkyl fumarate in a proportion of 0.01 to 0.1% by weight.

The present invention further provides a composition comprising one or more polyaspartic esters of the general formula (I)

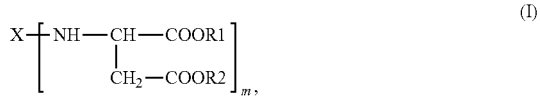

in which
- X is an m-valent organic radical, optionally containing one or more heteroatoms, as can be obtained by removing the primary amino groups from a corresponding polyamine that has (cyclo)aliphatically or araliphatically attached amino groups and is in the molecular weight range from 60 to 6000 g/mol, and which may contain further functional groups that are reactive toward isocyanate groups and/or inert at temperatures of up to 100° C.,
- R1 and R2 are identical or different organic radicals each having 1 to 18 carbon atoms,
- m is an integer >1, and one or more polyaspartic esters having a primary amino group that are of the general formula (II)

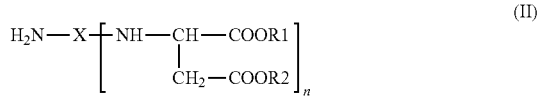

in which
- n is m−1,
- X and radicals R1 and R2 have the meanings defined above, characterized in that the proportion of the compound of the general formula (II) corresponds to from 1% to 20% of the GC surface area (measured as area-% in the gas chromatogram), the proportion of the two compounds of the general formula (I) and (II), wherein the sum of the GC surface areas of the two compounds of the general formula (I) and (II) is 100% and dialkyl fumarate is present in a proportion of 0.01 to 3% by weight.

Preference is given to the polyaspartic ester compositions according to the invention containing a proportion of 1% to 20%, preferably 4% to 20%, more preferably up to 4% to 15%, of the GC surface area (measured as area-% in the gas chromatogram) of the two compounds of the general formula (II) and (III) corresponds, wherein the sum of the GC surface areas of the two compounds of the general formula (I) and (II) is 100%.

The present invention particularly preferably and further provides a composition comprising one or more polyaspartic esters of the general formula (I),
in which
X is an m-valent organic radical optionally containing one or more heteroatoms, as obtained by removing primary amino groups from polyether polyamines having aliphatically attached primary amino groups, 1,2-diaminopropane, 1,4-diaminobutane, 1,5-diaminopentane, 1,6-diaminohexane, 1,5-diamino-2-methylpentane, 2,5-diamino-2,5-dimethylhexane, 2,2,4- and/or 2,4,4-trimethyl-1,6-diaminohexane, 1,11-diaminoundecane, 1,12-diaminododecane, 1-amino-3,3,5-trimethyl-5-aminomethylcyclohexane, 2,4- and/or 2,6-hexahydrotolylenediamine, 2,4'- and/or 4,4'-diaminodicyclohexylmethane or 3,3'-dimethyl-4,4'-diaminodicyclohexylmethane, R1 and R2 are identical or different alkyl radicals each having 1 to 8 carbon atoms,
m is an integer >1,
and
one or more polyaspartic esters having primary amino groups of the general formula (II), in which
n is m−1,
X and radicals R1 and R2 have the meanings defined above, characterized in that the proportion of the compound of the general formula (II) corresponds to from 4% to 20% of the GC surface area (measured as area-% in the gas chromatogram), the proportion of the two compounds of the general formula (I) and (II), wherein the sum of the GC surface areas of the two compounds of the general formula (I) and (II) is 100% and dialkyl fumarate is present in a proportion of 0.01 to 1% by weight.

The present invention most preferably and further provides a composition comprising one or more polyaspartic esters of the general formula (I), in which
X is an m-valent organic radical as can be obtained by removing primary amino groups from 3,3'-dimethyl-4,4'-diaminodicyclohexylmethane, 2,4'- and/or 4,4'-diaminodicyclohexylmethane, 1,5-diamino-2-methylpentane,
R1 and R2 are identical or different alkyl radicals selected from the group consisting of methyl, ethyl, propyl, isopropyl, butyl or isobutyl radicals,
m is 2,
and
one or more polyaspartic esters having primary amino groups of the general formula (II), in which
n is m−1,
X and radicals R1 and R2 have the meanings defined above, characterized in that the proportion of the compound of the general formula (II) corresponds to from 4% to 15% of the GC surface area (measured as area-% in the gas chromatogram), the proportion of the two compounds of the general formula (I) and (II), wherein the sum of the GC surface areas of the two compounds of the general formula (I) and (II) is 100% and dialkyl fumarate is present in a proportion of 0.01 to 0.1% by weight.

The present invention particularly preferably further provides a composition comprising one or more polyaspartic esters of the general formula
(I),
in which
X is an m-valent organic radical as can be obtained by removing primary amino groups from 3,3'-dimethyl-4,4'-diaminodicyclohexylmethane, 2,4'- and/or 4,4'-diaminodicyclohexylmethane, R1 and R2 are ethyl radicals,
m is 2,
and
one or more polyaspartic esters having a primary amino group that are of the general formula (II), in which
n is m−1,
X and radicals R1 and R2 have the meanings defined above,
characterized in that the proportion of the compound of the general formula (II) corresponds to from 4% to 15% of the GC surface area (measured as area-% in the gas chromatogram), the proportion of the two compounds of the general formula (I) and (II), wherein the sum of the GC surface areas of the two compounds of the general formula (I) and (II) is 100% and dialkyl fumarate is present in a proportion of 0.01 to 0.1% by weight.

The invention further provides a process for producing the composition comprising one or more polyaspartic esters of the general formula (I)

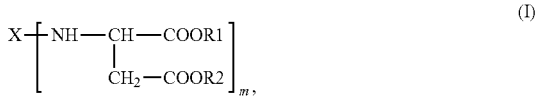
(I)

in which
X is an m-valent organic radical, optionally containing one or more heteroatoms, as can be obtained by removing the primary amino groups from a corresponding polyamine that has (cyclo)aliphatically or araliphatically attached amino groups and is in the molecular weight range from 60 to 6000 g/mol, and which may contain further functional groups that are reactive toward isocyanate groups and/or inert at temperatures of up to 100° C.,
R1 and R2 are identical or different organic radicals, preferably identical or different alkyl radicals each having 1 to 18 carbon atoms, and most preferably identical or different alkyl radicals each having 1 to 8 carbon atoms,
m is an integer >1,
and
one or more polyaspartic esters having a primary amino group that are of the general formula (II)

(II)

in which
n is m−1,
X and radicals R1 and R2 have the meanings defined above,
produced by reacting polyamines of the general formula (III),

(III)

in which X and m have the meaning defined above, with compounds of the general formula (IV)

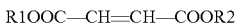 (IV), in which the radicals R1 and R2 have the meaning defined above,
characterized in that the resulting polyaspartic ester composition contains a proportion of the compound of the general formula (II) of from 1% to 20% of the GC surface area (measured as area-% in the gas chromatogram), which corresponds to the proportion of the two compounds of the general formula (I) and (II), wherein the sum of the GC surface areas of the two compounds of the general formula (I) and (II) is 100%, and dialkyl fumarate in a proportion of 0.01 to 3% by weight.

The present invention preferably further provides the process disclosed above for producing the composition comprising one or more polyaspartic esters of the general formula (I), in which
X is an m-valent organic radical, optionally containing one or more heteroatoms, as obtained by removing primary amino groups from polyether polyamines having aliphatically attached primary amino groups, 1,2-diaminopropane, 1,4-diaminobutane, 1,5-diaminopentane, 1,6-diaminohexane, 1,5-diamino-2-methylpentane, 2,5-diamino-2,5-dimethylhexane, 2,2,4- and/or 2,4,4-trimethyl-1,6-diaminohexane, 1,11-diaminoundecane, 1,12-diaminododecane, 1-amino-3,3,5-trimethyl-5-aminomethylcyclohexane, 2,4- and/or 2,6-hexahydrotolylenediamine, 2,4'- and/or 4,4'-diaminodicyclohexylmethane or 3,3'-dimethyl-4,4'-diaminodicyclohexylmethane,
R1 and R2 are identical or different alkyl radicals each having 1 to 8 carbon atoms,
m is an integer >1,
and
one or more polyaspartic esters having a primary amino group that are of the general formula (II), in which
n is m−1,
X and radicals R1 and R2 have the meanings defined above,
produced by reacting polyamines of the general formula (III), in which X and m have the meaning defined above, with compounds of the general formula (IV), in which the radicals R1 and R2 have the meaning defined above,
characterized in that the resulting polyaspartic ester composition contains a proportion of the compound of the general formula (II) of from 4% to 20% of the GC surface area (measured as area-% in the gas chromatogram), which corresponds to the proportion of the two compounds of the general formula (I) and (II), wherein the sum of the GC surface areas of the two compounds of the general formula (I) and (II) is 100%, and dialkyl fumarate in a proportion of 0.01 to 1% by weight.

The present invention preferably further provides the process disclosed above for producing the composition comprising one or more polyaspartic esters of the general formula (I), in which
X is an m-valent organic radical, as can be obtained by removing primary amino groups from 3,3'-dimethyl-4,4'-diaminodicyclohexylmethane, 2,4'- and/or 4,4'-diaminodicyclohexylmethane, 1,5-diamino-2-methylpentane,
R1 and R2 are identical or different alkyl radicals selected from the group consisting of methyl, ethyl, propyl, isopropyl, butyl or isobutyl radicals,
m is 2,
and
one or more polyaspartic esters having a primary amino group that are of the general formula (II), in which n is m−1, X and radicals R1 and R2 have the meanings defined above, produced by reacting polyamines of the general formula (III), in which X and m have the meaning defined above, with compounds of the general formula (IV), in which the radicals R1 and R2 have the meaning defined above, characterized in that the resulting polyaspartic ester composition contains a proportion of the compound of the general formula (II) of from 4% to 15% of the GC surface area (measured as area-% in the gas chromatogram), which corresponds to the proportion of the two compounds of the general formula (I) and (II), wherein the sum of the GC surface areas of the two compounds of the general formula (I) and (II) is 100%, and dialkyl fumarate in a proportion of 0.01 to 0.1% by weight.

The present invention preferably further provides the process disclosed above for producing the composition comprising one or more polyaspartic esters of the general formula (I), in which X is an m-valent organic radical as can be obtained by removing primary amino groups from 2,4'- and/or 4,4'-diaminodicyclohexylmethane, R1 and R2 are ethyl radicals, m is 2, and one or more polyaspartic esters having a primary amino group that are of the general formula (II), in which n is m−1, X and radicals R1 and R2 have the meanings defined above, produced by reacting polyamines of the general formula (III), in which X and m have the meaning defined above, with compounds of the general formula (IV), in which the radicals R1 and R2 have the meaning defined above, characterized in that the resulting polyaspartic ester composition contains a proportion of the compound of the general formula (II) of 4% to 15% of the GC surface area (measured as area-% in the gas chromatogram) that corresponds to the proportion of the two compounds of the general formula (I) and (II), wherein the sum of the GC surface areas of the two compounds of the general formula (I) and (II) is 100%, and dialkyl fumarate in a proportion of 0.01 to 0.1% by weight.

The process according to the invention for producing the composition comprising polyaspartic esters of the general formula (I) and one or more polyaspartic esters having primary amino groups of the general formula (II) is preferably carried out in two steps. In the first step, the compounds of the general formula (III) and (IV) are reacted at temperatures between 0° C. and 100° C., preferably 20 to 80° C., and more preferably 20 to 60° C., in a ratio of equivalents of primary amino groups in the compounds of the general formula (III) to C=C double bond equivalents in the compounds of the general formula (IV) of 1:1.2 to 1.2:1, but preferably 1:1.05 to 1.05:1, until the residual content of compounds of the general formula (IV) is from 2 to 15% by weight, preferably from 3 to 10% by weight.

In the second step, the unreacted fraction of the compounds of the general formula (IV) is removed by distillation.

Suitable conditions during the distillation are a pressure range between 0.01 and 2 mbar and a temperature of the bottom outflow on exiting the distillation apparatus of ≤170° C. and ≥ the temperature resulting from the following formula (V):

$$T(\text{bottom outflow}) = 27 \times \ln(p) + 150 \qquad (V)$$

where T(bottom outflow) is the temperature of the bottom outflow in ° C. and p is the pressure in the distillation apparatus in mbar.

Maintaining this pressure range ensures not only that moderate temperatures in the bottom outflow are sufficient for depletion of the dialkyl fumarate content to the desired degree, but that the process remains usable on an industrial scale. At lower pressure, the gas density becomes too low and the necessary equipment items consequently so large that the process becomes disadvantageous from an economic viewpoint.

The temperature of the bottom outflow is preferably ≤170° C., but at least 20 K above the temperature resulting from formula (V); more preferably it is between 20 K and 40 K above the temperature resulting from formula (V), but not above 170° C.

Compounds of the general formula (III) that are used in the process according to the invention are all known polyamines having primary amino groups that conform to the general formula (III). Examples include the following compounds: ethylenediamine, 1,2-diaminopropane, 1,4-diaminobutane, 1,5-diaminopentane, 2,5-diamino-2,5-dimethylhexane, 1,5-diamino-2-methylpentane (Dytek®A, DuPont), 1,6-diaminohexane, 2,2,4- and/or 2,4,4-trimethyl-1,6-diaminohexane, 1,11-diaminoundecane, 1,12-diaminododecane or triaminononane, etheramines such as 4,9-dioxadodecane-1,12-diamine, 4,7,10-trioxatridecane-1,13-diamine, or higher-molecular-weight polyether polyamines having aliphatically attached primary amino groups, for example those marketed under the Jeffamine® name by Huntsman. Also employable are aliphatic polycyclic polyamines such as tricyclodecanebismethylamine (TCD diamine) or bis(aminomethyl)norbornanes, aminofunctional siloxanes, for example diaminopropylsiloxane G10 DAS (from Momentive), oleoalkyl-based amines, for example Fentamine from Solvay, dimeric fatty acid diamines such as Priamine from Croda.

In the process according to the invention, preference is given to the use of polyamines of the general formula (III), in which m=2 and X is a cyclic hydrocarbon radical having at least one cyclic carbon ring. Examples of diamines that are usable with particular preference are 1-amino-3,3,5-trimethyl-5-aminomethylcyclohexane (IPDA), 2,4- and/or 2,6-hexahydrotolylenediamine (H6-TDA), isopropyl-2,4-diaminocyclohexane, and/or isopropyl-2,6-diaminocyclohexane, 1,3-bis(aminomethyl)cyclohexane, 2,4'-, and/or 4,4'-diaminodicyclohexylmethane, 3,3'-dimethyl-4,4'-diaminodicyclohexylmethane (Laromin® C 260, BASF AG), the isomeric diaminodicyclohexylmethanes substituted in the ring with a methyl group (=C-monomethyl-diaminodicyclohexylmethanes), 3(4)-aminomethyl-1-methylcyclohexylamine (AMCA), and also araliphatic diamines such as 1,3-bis(aminomethyl)benzene or m-xylylenediamine. In the process according to the invention, preference is also given to the use of polyamines of the general formula (III) selected from the following group: polyether polyamines having aliphatically attached primary amino groups, 1,2-diaminopropane, 1,4-diaminobutane, 1,5-diaminopentane, 1,6-diaminohexane, 1,5-diamino-2-methylpentane, 2,5-diamino-2,5-dimethylhexane, 2,2,4- and/or 2,4,4-trimethyl-1,6-diaminohexane, 1,11-diaminoundecane, 1,12-diaminododecane, 1-amino-3,3,5-trimethyl-5-aminomethylcyclohexane, 2,4- and/or 2,6-hexahydrotolylenediamine, 2,4'- and/or 4,4'-diaminodicyclohexylmethane or 3,3'-dimethyl-4,4'- diaminodicyclohexylmethane. Particular preference is given to 3,3'-dimethyl-4,4'-diaminodicyclohexylmethane, 2,4'- and/or 4,4'-diaminodicyclohexylmethane, 1,5-diamino-2-methylpentane, and very particular preference to the use of 2,4'- and/or 4,4'-diaminodicyclohexylmethane.

Particular preference is given to the polyaspartic ester compositions according to the invention in which X is organic radicals obtained by removing the primary amino groups from one of the polyamines of the general formula (III) selected from the following group: polyether polyamines having aliphatically attached primary amino groups, 1,2-diaminopropane, 1,4-diaminobutane, 1,5-diaminopentane, 1,6-diaminohexane, 1,5-diamino-2-methylpentane, 2,5-diamino-2,5-dimethylhexane, 2,2,4- and/or 2,4,4-trimethyl-1,6-diaminohexane, 1,11-diaminoundecane, 1,12-diaminododecane, 1-amino-3,3,5-trimethyl-5-aminomethylcyclohexane, 2,4- and/or 2,6-hexahydrotolylenediamine, 2,4'- and/or 4,4'-diaminodicyclohexylmethane or 3,3'-dimethyl-4,4'-diaminodicyclohexylmethane.

Most preferred are the polyaspartic ester compositions according to the invention in which X is organic radicals obtained by removing the primary amino groups from one of the polyamines of the general formula (III) selected from the following group: 3,3'-dimethyl-4,4'-diaminodicyclohexylmethane, 2,4'- and/or 4,4'-diaminodicyclohexylmethane, 1,5-diamino-2-methylpentane.

Preferred compounds of the general formula (IV) that are used in the process according to the invention are maleic or fumaric esters of the general formula (IV) in which R1 and R2 are identical or different organic radicals each having 1 to 18 carbon atoms. Preferably, R1 and R2 are independently linear or branched alkyl radicals having 1 to 8 carbon atoms. Examples of compounds of the general formula (IV) are the following compounds: dimethyl maleate, diethyl maleate, di-n-propyl or diisopropyl maleate, di-n-butyl maleate, di-2-ethylhexyl maleate or the corresponding fumaric esters. Particular preference is given to diethyl maleate.

The polyaspartic ester compositions according to the invention are valuable reaction partners for polyisocyanates in low-solvent or solvent-free two-component polyurethane systems.

The invention thus also provides for the use of the polyaspartic ester compositions according to the invention as a reactive component in two-component polyurethane systems or in the production of prepolymers. The two-component (2K) polyurethane systems comprising the polyaspartic ester compositions according to the invention may then be used as coating compositions in the production of coatings.

In addition to the components essential to the invention, the coating compositions essential to the invention may also employ auxiliaries customary in coating technology such as inorganic or organic pigments, other organic light stabilizers, free-radical scavengers, coatings additives such as dispersants, leveling agents, thickeners, defoaming agents and other auxiliaries, bonding agents, fungicides, bactericides, stabilizers or inhibitors and catalysts.

The coating compositions according to the invention are preferably used in the fields of OEM finishing of automobiles, refinishing of automobiles, coatings for large vehicles, coatings for plastics, general industrial coatings, coatings for floors and/or for wood/furniture.

The invention accordingly also further provides coated substrates obtainable using the polyaspartic ester compositions according to the invention.

EXPERIMENTAL

Raw Materials:
Vestamin PACM: a mixture of 2,4- and 4,4'-diaminodicyclohexylmethane, manufacturer: Evonik
Desmodur N 3600: a low-viscosity HDI trimer containing approx. 23% NCO and ≤0.25% free HDI, manufacturer: Covestro
Desmodur N 3900: a low-viscosity HDI trimer containing approx. 23.5% NCO and ≤0.25% free HDI, manufacturer: Covestro
Byk 331: polyether-modified polydimethylsiloxane surface additive, manufacturer: Byk
Tinuvin 292: a mixture of bis(1,2,2,6,6-pentamethyl-4-piperidyl)sebacate and methyl 1,2,2,6,6-pentamethyl-4-piperidylsebacate, a light stabilizer from BASF
Tinuvin 384-2: benzenepropanoic acid, 3-(2H-benzotriazol-2-yl)-5-(1,1-dimethylethyl)-4-hydroxy, $C_7$-$C_9$ branched and linear alkyl esters, a light stabilizer from BASF Methods:
Diethyl fumarate contents were quantitatively determined using a GC method with internal standard. An Agilent 6890 gas chromatograph with a standard GC capillary (100% polysiloxane phase) and FID detector were used. The injector temperature (split outlet) was 180° C.; helium was used as the carrier gas. The quantitation limit of this method was 300 ppm.

GC-MS analyses were carried out using an Agilent 6890 gas chromatograph and Agilent 5973 mass spectrum detector with standard ionization (electron impact) at 70 eV, a standard GC capillary (100% polysiloxane phase) and split injection at an injector temperature of 250° C. Evaluation of the gas chromatograms was in area-%.

All viscosity measurements were carried out using a Physica MCR 51 rheometer from Anton Paar Germany GmbH (DE) in accordance with DIN EN ISO 3219:1994-10.

NCO contents were determined titrimetrically in accordance with DIN EN ISO 11909:2007-05.

Hazen color index values were determined on a Lico 400 colorimeter from Hach Lange GmbH, Düsseldorf in accordance with DIN EN ISO 6271:2016-05

Amine values were determined titrimetrically in accordance with EN ISO 9702:1998 (perchloric acid method) with the exception that the results were expressed as the amine value. The amine value in mg KOH/g was calculated according to the following equation:

$$\text{Amine value} = \frac{(a-b) \times 5.61}{W}$$

a=volume of perchloric acid consumed in the main test, in milliliters, c=0.1 mol/l;
b=volume of perchloric acid consumed in the blank test, in milliliters, c=0.1 mol/l;
W=weight of sample, in grams Flow times were determined in accordance with DIN EN ISO 2431:2012-03, with the exception that a DIN 4 flow cup was used. The pot life was defined as the time corresponding to twice the flow time.

Drying determinations were carried out in accordance with DIN EN ISO 9117-5:2012-11.

For the determination of reactivity, the following gel-time measurement method was developed: The feedstocks (total amount 10 g) were weighed into a beaker and mixed for 15 seconds at 3000 rpm in a Speedmixer. Then, using a bent paperclip or a disposable pipette, the time taken for the mixture to be drawn into threads or to become solid was determined with a stopwatch.

Example 1 (Comparative Example)

Polyaspartic ester commercially available from Covestro under the name Desmophen NH 1420.
Material data:

| | |
|---|---|
| Monoamine of the formula (II) (GC-MS): | 4.0% |
| Diethyl fumarate (GC) | 2.9% by weight |
| Viscosity | 1220 mPas |
| Color index | 27 APHA |
| Amine value | 201 mg KOH/g |

Example 2 (Comparative Example)

341.8 g of Vestamin PACM was initially charged at 23° C. under dry nitrogen, with stirring. To this was added dropwise 839.4 g of diethyl maleate, ensuring that the temperature did not rise above 60° C. At the end of the addition, the temperature was adjusted to 45° C. and the mixture was stirred for one hour at 45° C. The mixture was then stored at 23° C. for 8 weeks. The content of diethyl fumarate after storage was 0.04% by weight. A light-colored product was obtained that had the following material data:

| | |
|---|---|
| Monoamine of the formula (II) (GC-MS): | 65.8% |
| Diethyl fumarate (GC) | 0.04% by weight |
| Viscosity | 690 mPas |
| Color index | 16 APHA |
| Amine value | 293 mg KOH/g |

Example 3 (Comparative Example)

341.8 g of Vestamin PACM was initially charged at 23° C. under dry nitrogen, with stirring. To this was added dropwise 1678.8 g of diethyl maleate, ensuring that the temperature did not rise above 60° C. At the end of the addition, the temperature was adjusted to 45° C. and the mixture was stirred for one hour at 45° C. The mixture was then stored at 23° C. for 24 hours. The content of diethyl fumarate after storage was 11.5% by weight. Diethyl fumarate was then distilled off at 120° C. and 0.2 mbar. A light-colored product was obtained that had the following material data:

| | |
|---|---|
| Monoamine of the formula (II) (GC-MS): | 25.4% |
| Diethyl fumarate (GC) | 0.05% by weight |
| Viscosity | 1330 mPas |
| Color index | 8 APHA |
| Amine value | 224 mg KOH/g |

Example 4

341.8 g of P Vestamin PACM was initially charged at 23° C. under dry nitrogen, with stirring. To this was added dropwise 1678.8 g of diethyl maleate, ensuring that the temperature did not rise above 60° C. At the end of the addition, the temperature was adjusted to 45° C. and the mixture was stirred for 2 hours at 45° C. The mixture was then stored at 23° C. for 7 weeks. The content of diethyl fumarate after storage was 2.7% by weight. Diethyl fumarate was then distilled off at 120° C. and 0.2 mbar. A light-colored product was obtained that had the following material data:

| | |
|---|---|
| Monoamine of the formula (II) (GC-MS): | 5.3% |
| Diethyl fumarate (GC) | 0.08% by weight |
| Viscosity | 1810 mPas |
| Color index | 19 APHA |
| Amine value | 203 mg KOH/g |

Example 5

341.8 g of Vestamin PACM was initially charged at 23° C. under dry nitrogen, with stirring. To this was added dropwise 1678.8 g of diethyl maleate, ensuring that the temperature did not rise above 60° C. At the end of the addition, the temperature was adjusted to 45° C. and the mixture was stirred for two hours at 45° C. The mixture was then stored at 23° C. for 30 hours. The content of after storage was 8.62% by weight. Diethyl fumarate was then distilled off at 120° C. and 0.2 mbar. A light-colored product was obtained that had the following material data:

| | |
|---|---|
| Monoamine of the formula (II) (GC-MS): | 13.2% |
| Diethyl fumarate (GC) | <0.03% by weight |
| Viscosity | 1650 mPas |
| Color index | 5 APHA |
| Amine value | 213 mg KOH/g |

Example 6

341.8 g of Vestamin PACM was initially charged at 23° C. under dry nitrogen, with stirring. To this was added dropwise 1678.8 g of diethyl maleate, ensuring that the temperature did not rise above 60° C. At the end of the addition, the temperature was adjusted to 45° C. and the mixture was stirred for one hour at 45° C. The mixture was then stored at 23° C. for 24 hours. The content of diethyl fumarate after storage was 8.85% by weight. Diethyl fumarate was then distilled off at 120° C. and 0.2 mbar. A light-colored product was obtained that had the following material data:

| | |
|---|---|
| Monoamine of the formula (II) (GC-MS): | 14.1% |
| Diethyl fumarate (GC) | 0.08% by weight |
| Viscosity | 1630 mPas |
| Color index | 5 APHA |
| Amine value | 214 mg KOH/g |

Before performance testing, the reactivity of selected polyaspartic esters was determined by the gel-time measurement method described above.

TABLE 1

Determination of reactivity by the gel-time measurement method

| Feedstock | Desmodur N 3600 | Desmodur N 3600 | Desmodur N 3600 | Desmodur N 3600 | Desmodur N 3600 |
|---|---|---|---|---|---|
| Sample weight | 4.18 | 4.88 | 4.22 | 4.18 | 4.18 |
| Feedstock | Example 1 | Example 2 | Example 3 | Example 5 | Example 6 |
| Sample weight | 5.82 | 5.11 | 5.78 | 5.82 | 5.82 |

TABLE 1-continued

Determination of reactivity by the gel-time measurement method

| Feedstock | Desmodur N 3600 | Desmodur N 3600 | Desmodur N 3600 | Desmodur N 3600 | Desmodur N 3600 |
|---|---|---|---|---|---|
| Time until: | | | | | |
| sample can be drawn into threads | 37 min | n.d.* | 5 min | 49 min | 52 min |
| the sample is solid | 65 min | n.d.* | 7 min | 88 min | 92 min |

*Gelation of sample in Speedmixer

It can be seen from table 1 that the inventive composition comprising polyaspartic esters from examples 5 and 6, despite having a higher content of polyaspartic esters having primary amino groups compared to the commercially available product, does not show a shortened gel time and is therefore suitable for coatings.

Testing in Coatings

Inventive polyaspartic ester compositions from examples 1 and 5 were tested in coating formulations.

Preparation of a Coating Base

To the amount of component A shown in table 2 were added the additives and the amount of butyl acetate shown in the table, and the mixture was stirred thoroughly.

Preparation of the Hardener Solution

To the amount of component B shown in table 2 was added the amount of butyl acetate shown in the table, and the mixture was stirred thoroughly.

Mixing of the coating base with the hardener and application:

The coating base described above and the hardener were combined and mixed thoroughly. The mixtures were then each applied with an air gun to coil-coating sheet precoated with black basecoat, flashed off for 10 min at room temperature, and then dried at room temperature and at 60° C. Brilliant, high-gloss coatings with a layer thickness of 50 μm were obtained.

An overview of the coating properties determined for the coatings is shown in table 3.

TABLE 2

Composition of the coating bases

| Temperature: 24° C. | Example 7 (inventive) | Example 8 (inventive) | Example 9 (comparative) |
|---|---|---|---|
| Air humidity: 48% | | | |
| Component A | | | |
| Example 5 | 43.77 | | |
| Example 4 | | 45.25 | |
| Example 1 | | | 47.24 |
| Byk 331 (10% in BA) | 0.08 | 0.08 | 0.08 |
| Tinuvin 292 (50% in BA) | 0.16 | 0.17 | 0.16 |
| Tinuvin 384-2 (50% in BA) | 0.33 | 0.33 | 0.33 |
| Butyl acetate | 21.34 | 20.00 | 16.19 |
| Component B | | | |
| Desmodur N 3900 (100%) | 29.75 | 29.42 | 30.65 |
| Butyl acetate | 1.57 | 1.75 | 2.35 |

TABLE 3

Coating properties of coatings

| Temperature: 24° C. | | Example 7 | Example 8 | Example 9 |
|---|---|---|---|---|
| Relative humidity: 48% | | | | |
| Solids content in % at spray viscosity (calc.) | | 73.4 | 74.9 | 81.1 |
| Flow time DIN 4 mm (sec) | 0 h | 17 | 16 | 17 |
| | 5' | 18 | 17 | 18 |
| | 10' | 19 | 18 | 20 |
| | 15' | 21 | 19 | 24 |
| | 20' | 23 | 20 | 27 |
| | 25' | 27 | 22 | 31 |
| | 30' | 32 | 25 | 40 |
| Drying (min) RT | T 1 | 13 | 12 | 15 |
| | T 3 | 27 | 25 | 30 |
| | T 4 | 40 | 40 | 45 |
| Layer thickness (μm) | | about 50 | about 50 | about 50 |
| Drying (min) 30'-60° C. | T 1 | immediately | immediately | immediately |
| | T 3 | 15 | 15 | 20 |
| | T 4 | 27 | 25 | 30 |
| Layer thickness (μm) | | about 50 | about 50 | about 50 |

Comparison of the coating properties shown in table 3 for the comparison coating (example 9) with those of the inventive coatings (examples 7 and 8) demonstrates that the inventive coatings dry more rapidly while having an unchanged pot life.

The invention claimed is:

1. A polyaspartic ester composition comprising one or more polyaspartic esters of the general formula (I)

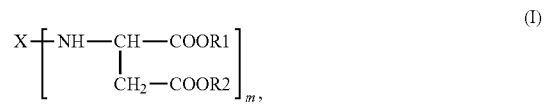

in which

X is an m-valent organic radical, optionally containing one or more heteroatoms obtained by removing the primary amino groups from a corresponding polyamine that has (cyclo)aliphatically or araliphatically attached amino groups and is in the molecular weight range from 60 to 6000 g/mol, and which comprises further functional groups that are reactive toward isocyanate groups and/or inert at temperatures of up to 100° C., R1 and R2 are identical or different organic radicals each having 1 to 18 carbon atoms, m is an integer >1, and one or more polyaspartic esters having a primary amino group that are of the general formula (II)

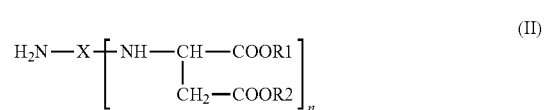

in which n is m−1,

X and radicals R1 and R2 have the meanings defined for the polyaspartic esters of the general formula (I), wherein a proportion of the polyaspartic esters of the general formula (II) corresponds to from 4% to 15% of a total GC surface area of the composition measured by gas chromatogram as area-%, wherein the total GC surface area is a sum of the individual surface areas of the polyaspartic esters of the general formulas (I) and (II) and is equal to 100%, and wherein the composition comprises dialkyl fumarate in a proportion of 0.01 to 1% by weight.

2. A process for producing the polyaspartic ester composition of claim 1 comprising: combining one or more polyaspartic esters of the general formula (I)

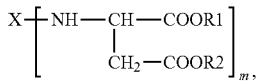 (I)

in which

X is an m-valent organic radical, optionally containing one or more heteroatoms obtained by removing the primary amino groups from a corresponding polyamine that has (cyclo)aliphatically or araliphatically attached amino groups and is in the molecular weight range from 60 to 6000 g/mol, and which comprises further functional groups that are reactive toward isocyanate groups and/or inert at temperatures of up to 100° C., R1 and R2 are identical or different organic radicals, preferably identical or different alkyl radicals each having 1 to 18 carbon atoms, m is an integer >1, with one or more polyaspartic esters having a primary amino group that are of the general formula (II)

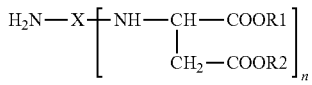 (II)

in which n is m−1,

X and radicals R1 and R2 have the meanings defined for the polyaspartic esters of the general formula (I), produced by reacting polyamines of the general formula (III),

 (III)

X─[NH$_2$]$_m$, in which X and m have the meaning defined for the polyaspartic esters of the general formula (I), with compounds of the general formula (IV)

R1OOC—CH═CH—COOR2     (IV), in which the radicals R1 and R2 have the meaning defined for the polyaspartic esters of the general formula (I);

and removing an unreacted proportion of the compound of the general formula (IV) by distillation, wherein the polyaspartic ester composition comprises a proportion of the polyaspartic ester of the general formula (II) of 4% to 15% of a total GC surface area measured by gas chromatogram as area-%, wherein the total GC surface area is a sum of the individual surface areas of the polyaspartic esters of the general formulas (I) and (II) and is equal to 100%, and wherein the composition comprises dialkyl fumarate in a proportion of 0.01 to 1% by weight.

3. A two-component polyurethane system, comprising the polyaspartic ester composition of claim 1 and a reactive component that is reactive towards the polyaspartic ester composition of claim 1.

4. A substrate coated with a polyaspartic ester composition as claimed in claim 1.

5. A prepolymer, comprising a reaction product of the polyaspartic ester composition of claim 1 with a reactive component that is reactive towards the polyaspartic ester composition of claim 1.

6. The polyaspartic ester composition of claim 1, wherein the composition has a platinum-cobalt color index of 5≤25.

* * * * *